(12) United States Patent
Nakatani et al.

(10) Patent No.: US 9,533,245 B2
(45) Date of Patent: Jan. 3, 2017

(54) FILTER DEVICE AND ANALYSIS DEVICE USING SAME

(71) Applicant: PANASONIC CORPORATION, Osaka (JP)

(72) Inventors: Masaya Nakatani, Hyogo (JP); Hiroaki Oka, Osaka (JP); Daniel Yazbeck, Cupertino, CA (US); Takeki Yamamoto, Hyogo (JP); Takahiro Nogami, Osaka (JP)

(73) Assignee: PANASONIC CORPORATION, Osaka (JP)

( * ) Notice: Subject to any disclaimer, the term of this patent is extended or adjusted under 35 U.S.C. 154(b) by 239 days.

(21) Appl. No.: 14/258,892

(22) Filed: Apr. 22, 2014

(65) Prior Publication Data

US 2014/0224724 A1     Aug. 14, 2014

Related U.S. Application Data

(63) Continuation of application No. PCT/JP2012/006805, filed on Oct. 24, 2012.

(30) Foreign Application Priority Data

Oct. 25, 2011     (JP) ................. 2011-234028

(51) Int. Cl.
*B01D 39/08*     (2006.01)
*G01N 33/49*     (2006.01)
(Continued)

(52) U.S. Cl.
CPC ............ *B01D 39/086* (2013.01); *B01J 20/103* (2013.01); *B01J 20/283* (2013.01); *B01J 20/286* (2013.01);
(Continued)

(58) Field of Classification Search
CPC ...... B01D 15/34; B01D 39/086; B01J 20/103; B01J 20/28038; B01J 20/283; B01J 20/286; B01J 20/3246; B01J 2220/54; B01L 3/502753; B01L 3/5635; D04H 1/4218; D04H 1/4326; D04H 1/54; G01N 1/10; G01N 2001/4088; G01N 2021/0325
(Continued)

(56) References Cited

U.S. PATENT DOCUMENTS 5,453,116 A * 9/1995 Fischer ............... B01D 39/086
55/341.2
6,267,898 B1   7/2001 Fukuda et al.
(Continued)

FOREIGN PATENT DOCUMENTS

JP     H11-12180 A     1/1999
JP     H11-12181 A     1/1999
(Continued)

OTHER PUBLICATIONS

Chen et al., "Protein Adsorption separation using glass fiber membranes modified with short-chain organosilicon derivatives", Journal of Membrane Science (Nov. 15, 2007), vol. 305, issues 1-2, pp. 125-135.*
(Continued)

*Primary Examiner* — Dirk Bass
(74) *Attorney, Agent, or Firm* — McDermott Will & Emery LLP (57) ABSTRACT

A filter device of the present disclosure includes at least a sheet-shaped fiber structure having a plurality of fibers made of amorphous silicon dioxide, wherein the plurality of fibers are tangled and thus connected together to form voids in the sheet-shaped fiber structure. A filter device of the present disclosure corresponds to an analysis device including: a
(Continued)

substrate; a flow path formed on the substrate; and a sheet-shaped fiber structure provided on the inner wall of the flow path, wherein the sheet-shaped fiber structure includes a plurality of fibers made of amorphous silicon dioxide, and the plurality of fibers are tangled and thus connected together to form voids in the sheet-shaped fiber structure.

12 Claims, 8 Drawing Sheets

(51) Int. Cl.
| | |
|---|---|
| D04H 1/4218 | (2012.01) |
| D04H 1/4326 | (2012.01) |
| D04H 1/54 | (2012.01) |
| B01J 20/28 | (2006.01) |
| B01J 20/283 | (2006.01) |
| B01J 20/286 | (2006.01) |
| B01J 20/32 | (2006.01) |
| B01J 20/10 | (2006.01) |
| G01N 21/05 | (2006.01) |
| G01N 1/40 | (2006.01) |
| B01L 3/00 | (2006.01) |
| B01D 15/34 | (2006.01) |
| G01N 21/03 | (2006.01) |

(52) U.S. Cl.
CPC ....... *B01J 20/28038* (2013.01); *B01J 20/3246* (2013.01); *D04H 1/4218* (2013.01); *D04H 1/4326* (2013.01); *D04H 1/54* (2013.01); *B01D 15/34* (2013.01); *B01J 2220/54* (2013.01); *B01L 3/502753* (2013.01); *B01L 3/5635* (2013.01); *G01N 21/05* (2013.01); *G01N 33/491* (2013.01); *G01N 2001/4088* (2013.01); *G01N 2021/0325* (2013.01)

(58) Field of Classification Search
USPC .................................. 210/323.1, 335, 500.1
See application file for complete search history.

(56) References Cited

U.S. PATENT DOCUMENTS

| | | | |
|---|---|---|---|
| 6,485,856 | B1 | 11/2002 | Brown et al. |
| 7,537,703 | B2 | 5/2009 | Nakajima et al. |
| 2006/0093740 | A1 | 5/2006 | Park et al. |
| 2008/0249326 | A1 | 10/2008 | Nakajima et al. |
| 2011/0232794 | A1 | 9/2011 | Nakatani et al. |

FOREIGN PATENT DOCUMENTS

| | | |
|---|---|---|
| JP | 2001-032162 A | 2/2001 |
| JP | 2002-154819 A | 5/2002 |
| JP | 2002-239317 A | 8/2002 |
| JP | 2004-061230 A | 2/2004 |
| JP | 2006-136878 A | 6/2006 |
| JP | 2007-216123 A | 8/2007 |
| WO | 2006/001300 A1 | 1/2006 |
| WO | 2010/082279 A1 | 7/2010 |

OTHER PUBLICATIONS

International Search Report issued in International Application No. PCT/JP2012/006805 with Date of mailing Feb. 12, 2013, with English Translation.

English translation of Notification of Transmittal of Translation of the International Preliminary Report on Patentability and Written Opinion issued in International Application No. PCT/JP2012/006805 dated May 8, 2014.

* cited by examiner

FILTER DEVICE AND ANALYSIS DEVICE USING SAME

CROSS-REFERENCE TO RELATED APPLICATIONS

This is a continuation application of International Application No. PCT/JP2012/006805, with an international filing date of Oct. 24, 2012, which claims priority of Japanese Patent Application No. 2011-234028 filed on Oct. 25, 2011, the contents of which is incorporated herein by reference.

BACKGROUND (1) Field of the Invention

The present disclosure relates to a sheet-shaped fiber structure made of fibrous silicon dioxide. The present disclosure also relates to a filter device as a part of a microreactor, a chemical chip, a biochip, a lab-on-a-chip, a nanochip, a chromatograph, or the like, which includes a sheet-shaped fiber structure for use in extracting only a specific material from a solution, and also relates to an analysis device using such a filter device.

(2) Description of Related Art

A filter device, as an example of application using a sheet-shaped fiber structure, aims to separate only a specific material (object to be examined) from a sample containing a plurality of materials, and is needed in a variety of fields.

For example, the surface of a first substrate made of quartz is subjected to a chemical treatment such as dry etching or wet etching, or a processing using a laser beam, an ion beam or energy ray irradiation to form a plurality of island-shaped columns. Subsequently, a second substrate made of silicon is bonded to the first substrate in such a manner that the columns are sealed between the substrates. The interstices between the island-shaped columns sealed between the first and second substrates are used as filter flow paths, as shown in Japanese Patent Laid-Open Publication No. 2002-239317.

Also disclosed is a device including a first substrate and a flow path groove formed on the surface of the first substrate, as shown in International Patent Publication No. WO 2010/082279. According to the device, a fibrous layer including a plurality of fibrous projections is provided in the flow path groove and located to its opening.

Also disclosed is a material for removing leukocytes, which contains 0.5% by weight or more and less than 50% by weight of ultra fine fibers each having a diameter of 0.02 µm or more and less than 0.8 µm, as shown in Japanese Patent Laid-Open Publication No. 11-12181. According to the material, the ultra fine fibers form a network structure having a circularity of 1.7 or less and an equivalent circle diameter of 1 µm or more and less than 20 µm.

Also disclosed is a member for removing leukocytes, which contains 5% by weight or more and less than 20% by weight of ultra fine fibers each having a diameter of 0.1 µm or more and less than 0.6 µm, as shown in Japanese Patent Laid-Open Publication No. 11-12180. According to the member, the ultra fine fibers have a degree of curvature of 1.2 or more An analysis chip, as an example of application using a filter device, conventionally has purposes such as purifying or isolating a very small amount of a product and analyzing components, and generally includes a column tube and a silica gel which is a column filler packed as a solid phase in the column. A known method for producing the silica gel is a method for producing a porous inorganic material by a sol-gel reaction using, as a raw material, an oxide material containing an organic compound such as an alkoxide. Specifically, the silica gel is produced as follows. A silica sol is formed by hydrolyzing, in the presence of an acid, an alkoxysilane in water or a mixed solution of water and an alcohol. The resulting silica sol is added to an oil-based dispersion medium including an aromatic hydrocarbon such as benzene, toluene, xylene, or ethylbenzene and an emulsifier such as a long-chain organic carboxylic acid or a surfactant. The mixture is stirred using a mixer such as a homomixer, and the resulting emulsion is formed into a gel. This production method is one of the most easily practicable methods and thus performed preferably. The silica gel produced by this method is used as a high-performance liquid chromatography filler because it has distinctive surface physical properties, as shown in International Patent Publication No. WO 2006/001300.

SUMMARY

In the above configurations, it is difficult to achieve efficient separation. Particularly when the content of the object to be detected is low, it is difficult to detect only the specific material (the object to be detected) from a sample solution containing a large number of materials by using the conventional filter device with a sheet-shaped fiber structure. It is also difficult to extract the specific material from a small amount of a solution containing a large number of materials. This results in low separation efficiency.

The conventional silica gel-based column for chromatography is a relatively large column having a diameter of 2 mm and a length of 10 cm because of the silica gel particle size and the separative power, and requires a solution for separation in an amount as large as 50 to 100 mL per analysis even in a liquid phase. It also requires an analysis time of about 60 minutes. This results in low analysis efficiency during measurement.

One non-limiting and exemplary embodiment provides improved separation efficiency during measurement.

In one general aspect, the techniques disclosed here feature: a filter device including at least a sheet-shaped fiber structure having a plurality of fibers made of amorphous silicon dioxide, wherein the plurality of fibers are tangled and thus connected together to form voids in the sheet-shaped fiber structure.

In another general aspect, the techniques disclosed here feature: an analysis device including a substrate, a flow path formed on the substrate, and a sheet-shaped fiber structure provided on the inner wall of the flow path, wherein the sheet-shaped fiber structure has a plurality of fibers made of amorphous silicon dioxide, and the plurality of fibers are tangled and thus connected together to form voids in the sheet-shaped fiber structure.

The sheet-shaped fiber structure of the present disclosure is made of amorphous silicon dioxide having a very high purity, and thus has a high heat resistance of 1,000° C. or higher. Specifically, the sheet structure is not damaged even when the filter device is subjected to a surface treatment using a heat treatment.

Since silicon dioxide is a material having a high alkali resistance and a high acid resistance, the sheet structure is not damaged even when it is subjected to a surface treatment using a chemical treatment.

In addition, its amorphous structure has flexibility higher than that of crystal fibers. Thus, the sheet structure is not damaged even when subjected to bending, pressing, or the like.

Therefore, the filter device including the sheet-shaped fiber structure of the present disclosure can be made smaller and reduce the time required for separation.

Therefore, the analysis device including the sheet-shaped fiber structure of the present disclosure can be made smaller and reduce the time required for separation.

The smaller analysis device allows analysis to be performed with a smaller amount of solvent and thus makes it possible to reduce the amount of the solvent. This can result in higher analysis efficiency.

Additional benefits and advantages of the disclosed embodiments will be apparent from the specification and figures. The benefits and/or advantages may be individually provided by the various embodiments and features of the specification and drawings disclosure, and need not all be provided in order to obtain one or more of the same.

BRIEF DESCRIPTION OF DRAWINGS

The present disclosure will become readily understood from the following description of non-limiting and exemplary embodiments thereof made with reference to the accompanying drawings, in which like parts are designated by like reference numeral and in which.

DETAILED DESCRIPTION

According to a first aspect, a filter device including at least a sheet-shaped fiber structure having a plurality of fibers made of amorphous silicon dioxide, wherein the plurality of fibers are tangled and thus connected together to form voids in the sheet-shaped fiber structure.

Further, as a filter device of a second aspect, in the first aspect, the sheet-shaped fiber structure may have connection sites formed by partially bonded fibers, and the fibers are partially bonded together at partially fused fibers.

Further, as a filter device of a third aspect, in the first aspect, each of the fibers may have a length of 1 µm or more and 500 µm or less.

Further, as a filter device of a fourth aspect, in the first aspect, a maximum distance between the fibers adjacent to each other may be 1 µm or more and 50 µm or less.

Further, as a filter device of a fifth aspect, in the first aspect, each of the fibers may have a diameter of 0.01 µm or more and 1 µm or less.

Further, as a filter device of a sixth aspect, in the first aspect, each of the fibers has a surface modified with a water-repellent film.

Further, as a filter device of a seventh aspect, in the first aspect, at least a surface part of each of the fibers may be doped with a nitrogen atom.

Further, as a filter device of a eighth aspect, in the seventh aspect, the concentration of the nitrogen atom dopant may be the highest at the surface part and decrease as it goes to a central part of each of the fibers, and the nitrogen atom may be absent at least at and near a most central part of each of the fibers.

Further, as an analysis device of ninth aspect, an analysis device including:

a flow path; and the filter device according to the first aspect provided in the flow path.

Further, as an analysis device of tenth aspect, in the ninth aspect, the sheet-shaped fiber structure has a functional group formed on a surface thereof, and the functional group is selected from a group of an octyl group, an octadecyl group, a docosyl group, and a triacontyl group.

Further, as an analysis device of eleventh aspect, in the ninth aspect, further comprising a plurality of the sheet-shaped fiber structures.

Further, as an analysis device of twelfth aspect, in the ninth aspect, the plurality of the sheet-shaped fiber structures include:

a first sheet-shaped fiber structure coated hydrophilically; and a second sheet-shaped fiber structure coated hydrophobically, and the first and second sheet-shaped fiber structures are alternately stacked.

Further, as an analysis device of thirteenth aspect, in the ninth aspect, the flow path has a diameter of 10 µm to 1,000 µm.

Further, as an analysis device of fourteenth aspect, in the ninth aspect, the flow path has a flow inlet provided with a fluid control mechanism.

Further, as an analysis device of fifteenth aspect, in the ninth aspect wherein the flow path has an end part provided with an optical path for optical analysis.

Appropriate examples are explained below in order to further clarify constituents and effects of the present disclosure. A preferred embodiment of the present disclosure is demonstrated hereinafter with reference to the accompanying drawings. It will be understood that the embodiments are not intended to limit the present disclosure.

(Embodiment 1)

Hereinafter, a sheet-shaped fiber structure of amorphous silicon dioxide in embodiment 1 of the present disclosure will be described with reference to the drawings.

Figure 1A:
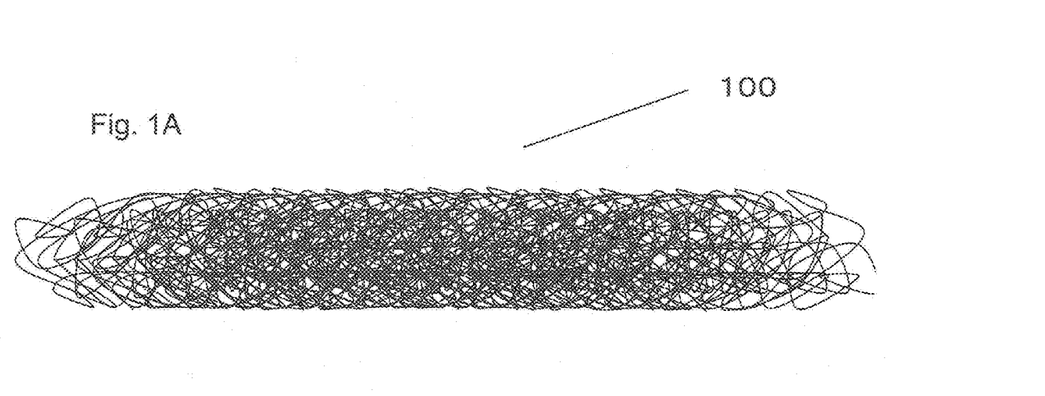
FIG. 1A is a cross-sectional view of a sheet-shaped fiber structure in embodiment 1.
Figure 2:
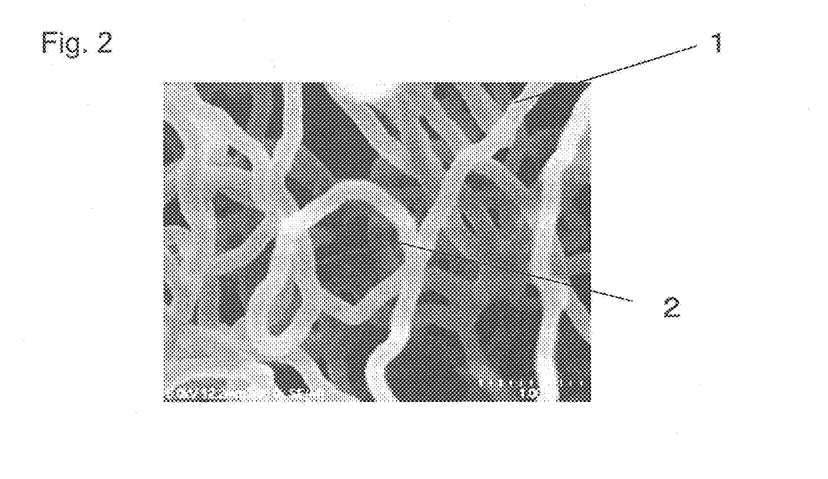
FIG. 2 is a SEM photograph of a principal part of the sheet-shaped fiber structure in embodiment 1.

FIG. 1A is a cross-sectional view of the sheet-shaped fiber structure in embodiment 1, and FIG. 2 is a photograph of a scanning electron microscope (SEM) image showing the surface state of the sheet-shaped fiber structure.

Figure 1B:
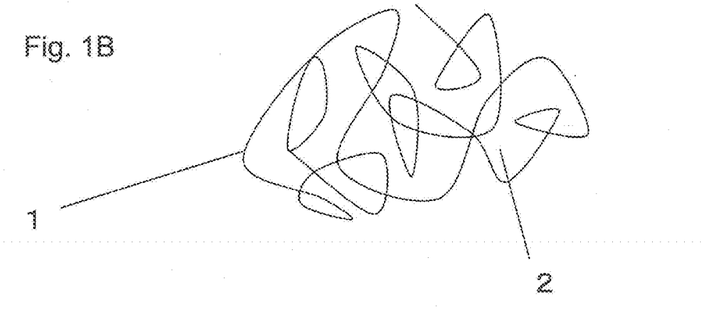
FIG. 1B is an enlarged view of a principal part of the sheet-shaped fiber structure in embodiment 1.

As shown in FIGS. 1A, 1B and FIG. 2, a sheet-shaped fiber structure 100 includes fibers 1 made of amorphous silicon dioxide (hereinafter, simply referred to as "silicon dioxide"), in which the fibers 1 are tangled and connected together to form voids 2 for allowing solutions, solid materials, and other materials to pass therethrough. The fibers 1 are tangled and densely packed together in a moderately curled state.

Figure 3:
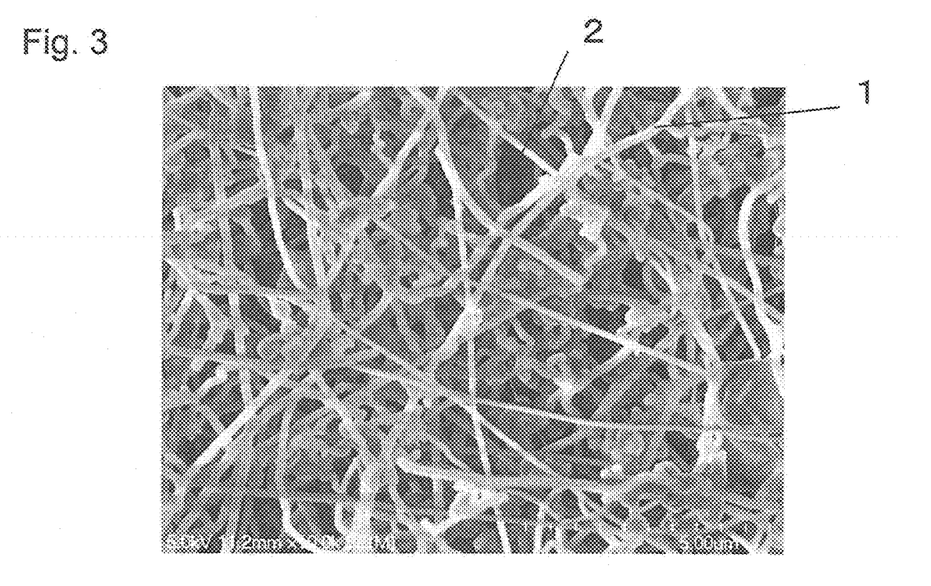
FIG. 3 is a SEM photograph of a principal part of the sheet-shaped fiber structure in embodiment 1.
Figure 4:
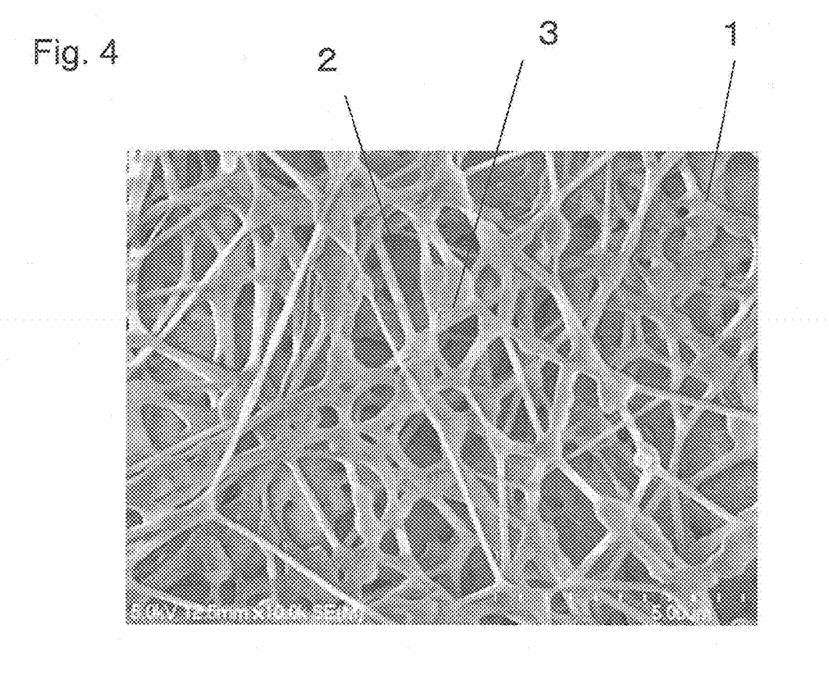
FIG. 4 is a SEM photograph of a principal part of the sheet-shaped fiber structure in embodiment 1.

Also, as shown in FIG. 3, the fibers 1 are tangled and densely packed together in a moderately curled state. As shown in FIG. 4, the fibers 1 are connected at connection sites 3 where the fibers 1 are partially fused together. This makes the fibers 1 more strongly linked together. When the connection sites 3 are formed in this manner, the adjacent fibers 1 are supported each other, so that the structure is stronger than the corresponding structure without the connection sites 3.

Next, an example of a method for manufacturing the sheet-shaped fiber structure will be described.

First, particles or a substrate made of Si as a raw material is provided. The raw material and a gas containing at least oxygen are mixed and then heated at 1,000 to 1,500° C. with a heater or the like. The raw material evaporates when reaching near the boiling or sublimation point of the raw material. The evaporating raw material is bonded to oxygen in the gas to form silicon suboxide (SiO), which then aggregates and captures oxygen in the atmosphere to form silicon dioxide ($SiO_2$). The resulting silicon dioxide ($SiO_2$) is deposited in the form of fibers 1. As used herein, the term "near the boiling or sublimation point of the raw material" refers to the temperature at which the raw material changes into gas under the surrounding pressure.

If a material serving as a nucleus is present around the formed SiO, the aggregation can easily occur, and the capture of oxygen from the atmosphere can result in efficient deposition of the fibers 1. A metal such as Pt, Fe, Co, Ni, or Au may be used as the material serving as a nucleus, and the type of the metal is not restricted. It will be understood that the material serving as a nucleus is not always necessary.

When the pressure during heating is set lower than atmospheric pressure, the raw material can have a lower boiling or sublimation point to evaporate easily, so that more fibers 1 can be formed. Specifically, the fibers 1 can be produced with higher productivity when the temperature is raised in a state where oxygen is removed as much as possible and the raised temperature is maintained under a low oxygen partial pressure such as $10^{-2}$ Pa to several thousand Pa with a small amount of oxygen added.

The fibers 1 deposited in this manner are tangled and layered together to form the sheet-shaped fiber structure 100. In this time, the sheet can be formed as the fibers 1 are growing, or the sheet can be formed after the fibers 1 have grown and the fibers 1 have been formed. Such conditions depend on the temperature at which the fibers 1 are formed.

When the sheet-shaped fiber structure 100 is heated at about 1,100° C. or higher, the sheet-shaped fiber structure 100 undergoes thermal fusion. The thermally fused $SiO_2$ fibers are bonded together, if they are adjacent and in contact with one another in a cooling process, so that a sheet-shaped fiber structure 100 having a plurality of connection sites 3 as shown in FIG. 3 is formed. The sheet-shaped fiber structure 100 with such connection sites has voids 2 and thus can have a large surface area. In addition, since the fibers 1 support one another, the structure is stronger than the corresponding structure without the connection sites 3.

The connection sites 3 can also be formed as the fibers 1 are growing. The formation of the connection sites 3 depends on the temperature at which the fibers 1 are formed. Particularly when a silicon substrate is used as the raw material, the fusion and the formation of the connection sites 3 easily occurs at the surface where the substrate and the fibers 1 come into contact together in the process of forming the fibers 1 because the fibers 1 are densely packed at the surface.

Besides oxygen, a gas having an oxidizing effect (in other words, capable of supplying oxygen), such as dinitrogen monoxide ($N_2O$) or carbon monoxide (CO), may also be used for forming the fibers 1. However, these gases, which contain an impurity other than oxygen, affect the process of forming the fibers 1 and the sheet-shaped fiber structure 100. Therefore, when these gases are used, it is necessary to appropriately control the concentration, the temperature, and the pressure.

The deposition of the fibers 1 may be varied dependent on the size of each of the fibers 1, the pressure of the atmosphere during the formation of the fibers 1, the oxygen concentration of the atmosphere, the temperature of the atmosphere, or other factors. Therefore, these conditions can be changed so that the fibers 1 and the sheet-shaped fiber structure 100 can be formed with the desired shape. The diameter (thickness) of each of the fibers 1 can be changed in a range of 0.01 μm or more and 1 μm or less. The length of each of the fibers 1 can be changed in a range of 1 μm or more and 500 μm or less.

The amorphous silicon dioxide has a very large surface area at the region where the sheet-shaped fiber structure 100 formed in this manner has a plurality of the fibers 1. On the other hand, a large number of the voids 2 are present around the amorphous silicon dioxide. The sheet-shaped fiber structure 100 includes the fibers 1 made of amorphous silicon dioxide and the voids 2. In this embodiment, the voids 2 make it possible to provide a filter function.

The sheet-shaped fiber structure 100 can be used at high temperatures and high oxygen concentrations. As shown in FIG. 3, a network structure can be easily formed through thermal fusion, and therefore, the sheet-shaped fiber structure 100 has the feature that its strength can be further increased, which cannot be achieved using carbon fibers.

Figure 5:
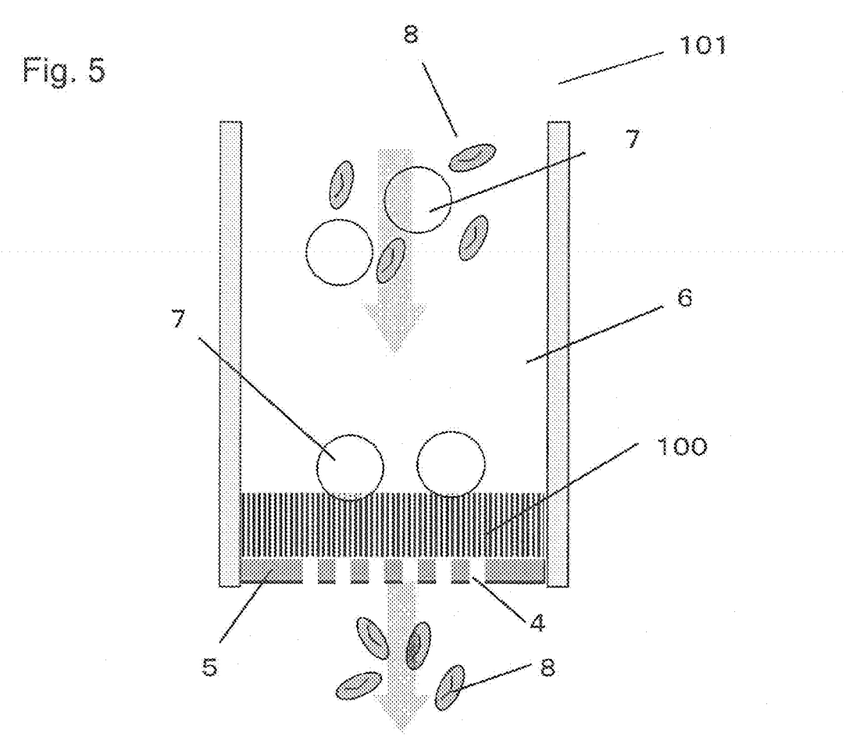
FIG. 5 is a schematic cross-sectional view showing use of a filter device in embodiment 1.
Figure 6:
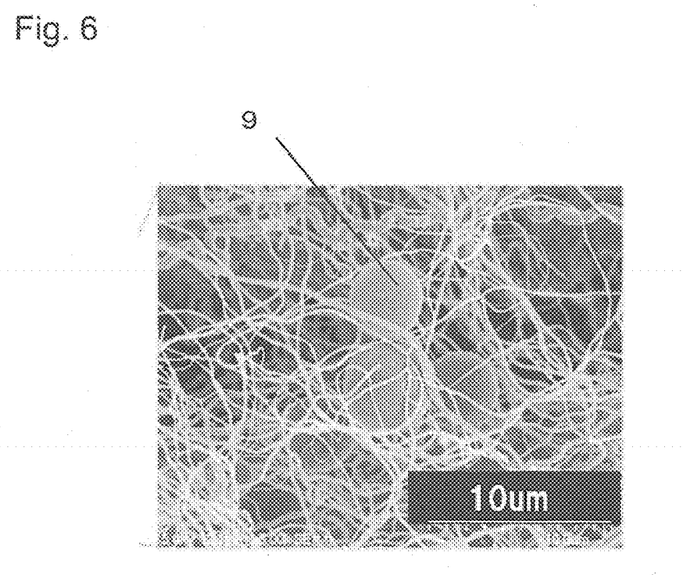
FIG. 6 is a SEM photograph of a principal part of the filter device in embodiment 1.

The sheet-shaped fiber structure 100 may be sealed in a fluid supply path such as a glass capillary or a PEEK tube to form a filter device 101. In this manner, filters for various types of solutions can be easily formed. FIG. 5 is a schematic diagram showing that the sheet-shaped fiber structure 100 is placed in a frame 5 having a plurality of through holes 4 and that the frame 5 is sealed in the front end part of a glass capillary 6. In this manner, a filter device 101 can be obtained, in which, for example, when a solution containing a mixture of leukocytes 7 and erythrocytes 8 is injected from the upper end of the capillary 6, the sheet-shaped fiber structure 100 can capture only the leukocytes 7 while selectively allowing the erythrocytes 8 to pass therethrough. The leukocytes 7 are captured by the sheet-shaped fiber structure 100 because only the leukocytes 7 have, on their surface, a specific protein that possesses the property of being easily adsorbed onto SiOH groups and the like on the surface of the sheet-shaped fiber structure 100. In addition to SiOH groups, various types of molecular structures can be attached to the surface of the sheet-shaped fiber structure 100. It is therefore preferable that various types of molecular structures be selected depending on the material to be captured by the filter. Also in this case, the sheet-shaped fiber structure 100 has a nano-scale bent fiber structure, and it is extremely advantageous that the materials of the structure is mainly made of silicon dioxide ($SiO_2$). Specifically, the materials have an excellent chemical resistance and heat resistance, which means that there are few limits on process conditions such as chemical and temperature used when various types of molecular structures are attached to the surface. The sheet-shaped fiber structure 100, which is made of nano-scale bent fibers, also has a large surface area and can capture particles (the material 9 to be separated by filtration) by twining around them as in the capturing shown in FIG. 6. Thus, the sheet-shaped fiber structure 100 has stronger capturing ability.

In FIG. 5, the filter device 101 includes the frame 5 having a plurality of through holes 4 and the sheet-shaped fiber structure 100 provided in the frame 5. The frame 5 may also be provided with a holder (not shown). The addition of the holder makes easier the joining during the insertion into the capillary 6. The addition of the holder also makes it possible to increase the strength of the main body of the frame 5. Therefore, it is preferred to provide the holder.

Figure 7:
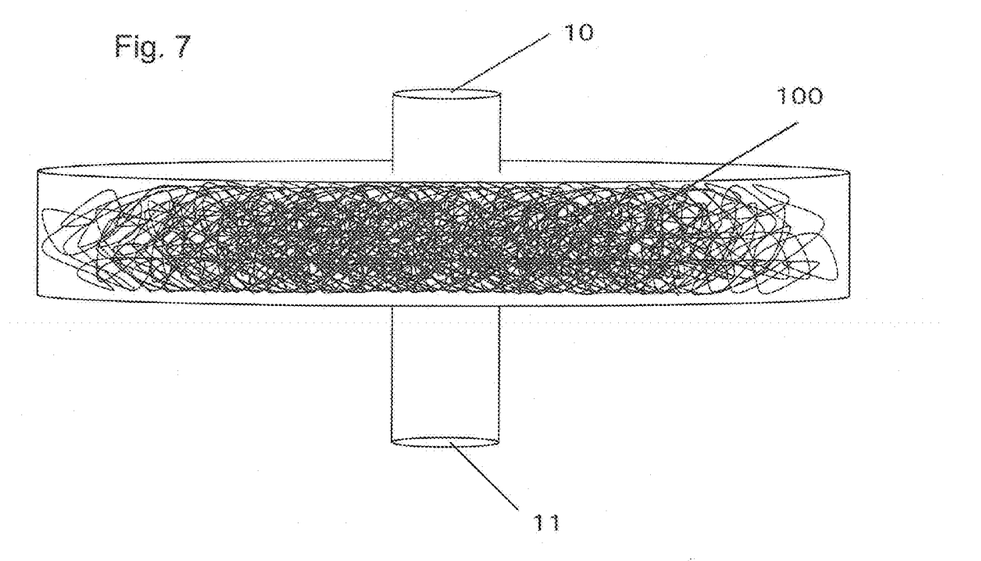
FIG. 7 is a cross-sectional view of the filter device in embodiment 1.

In FIG. 5, the filter device 101 has the sheet-shaped fiber structure 100 provided in the frame 5 having a plurality of through holes 4 formed. However, the formation of the frame 5 is not always necessary, and as shown in FIG. 7, the sheet-shaped fiber structure 100 only has to be interposed between a flow inlet 10 and a flow outlet 11. In this case, a flow path structure (not shown) is provided between the flow inlet 10 and the sheet-shaped fiber structure 100 so as to allow a solution to uniformly pass through the sheet-shaped fiber structure 100 when the solution is injected from the flow inlet 10. The filter having such an interposed flow path structure is common and will not be described more in this section.

Figure 8:
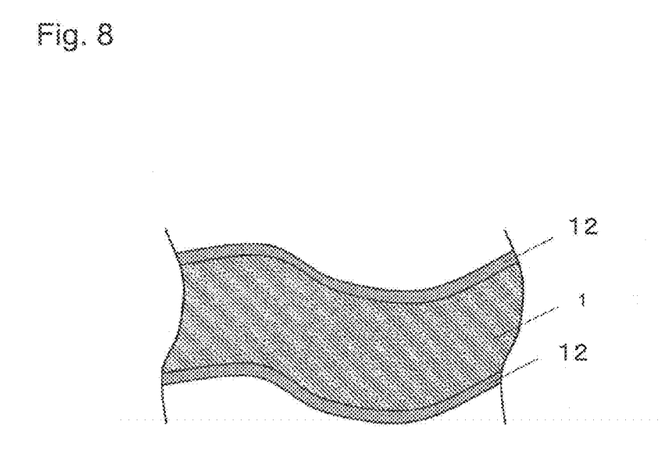
FIG. 8 is a cross-sectional view of the sheet-shaped fiber structure in embodiment 1.

As shown in FIG. 8, the surface of each of the fibers 1 in the prepared sheet-shaped structure 100 may also be modified by a water-repellent film 12. The water-repellent film 12 can be, for example, made with a polymer having $CF_2$ chains connected, a CF group-containing fluorine compound, an alkylsilyl group, a fluorosilyl group, or a long-chain alkyl group. The water-repellent film 12 can be formed on the surface of each of the fibers 1 by modifying the surface of each of the fibers 1 with a chemical having a water-repellent effect.

The filter device 101 having the highly-water-repellent sheet-shaped fiber structure 100 is particularly effective in filtering a hydrophobic solvent solution. When the sheet-shaped fiber structure 100 is hydrophilic, a hydrophobic solvent cannot enter the sheet-shaped fiber structure 100 provided in the filter device 101. When the sheet-shaped fiber structure 100 is modified to be hydrophobic, however, filtering of such a solvent can be achieved efficiently.

The sheet-shaped fiber structure 100 of the present disclosure is advantageous in such a case where the surface of the sheet-shaped fiber structure 100 is to be made hydrophobic because its structural materials is mainly made of silicon dioxide. This means that there are few limitations on chemicals and process conditions for the formation of the water-repellent surface because silicon dioxide has an excellent chemical resistance and heat resistance.

Nitrogen atoms may be doped from the surface part of each of the fibers 1 so that the molecular composition of the surface of each of the fibers 1 can be modified. Specifically, the surface of each of the fibers 1 can include SiN bonds or SiON bonds. The amorphous silicon dioxide as a main component of each of the fibers 1 may be heated at around 1,000° C. in an $NH_3$ gas atmosphere so that the surface of each of the fibers 1 can be doped with nitrogen atoms to have at least 5% of Si—O—N bonds or Si—N bonds. Si—O—N bonds or Si—N bonds are more stable than Si—O—H bonds or Si—O—Si bonds usually present on the surface of amorphous silicon dioxide, and therefore have the advantage that they allow stable adsorption of the material 9 (to be separated by filtration) on the surface of each of the fibers 1 regardless of how the filter device 101 changes over time.

Figure 9:
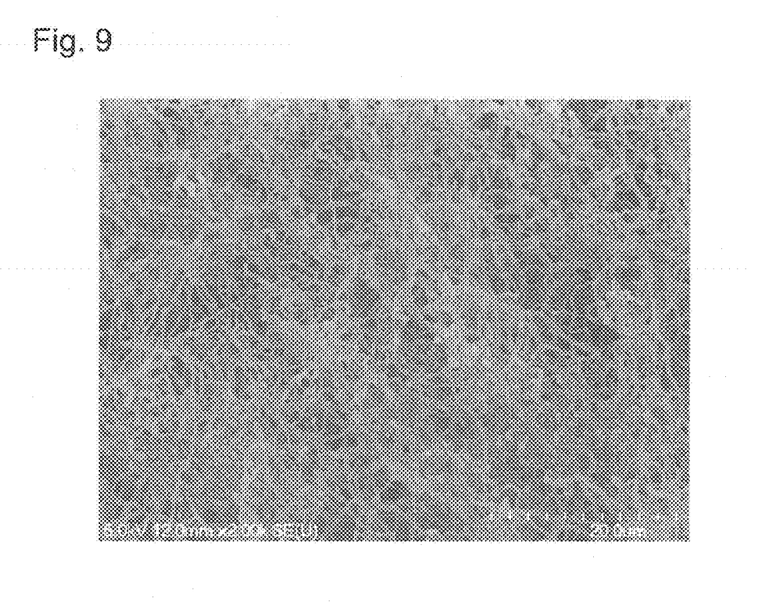
FIG. 9 is a SEM photograph of a principal part of the sheet-shaped fiber structure in embodiment 1 after a nitriding treatment.

For example, the sheet-shaped fiber structure 100 having the fibers 1 made of silicon dioxide was baked in an $NH_3$ gas atmosphere so that a nitriding treatment was performed, in which the surface and inner part of each of the fibers 1 were doped with nitrogen. FIG. 9 is a SEM photograph of a principal part of the nitrided sheet-shaped fiber structure in embodiment 1. As shown in FIG. 9, also after the nitriding treatment, a plurality of fibers 1 are tangled and connected together to form voids 2 with no change from the shape of each of the fibers 1 before the nitriding treatment.

Figure 10:
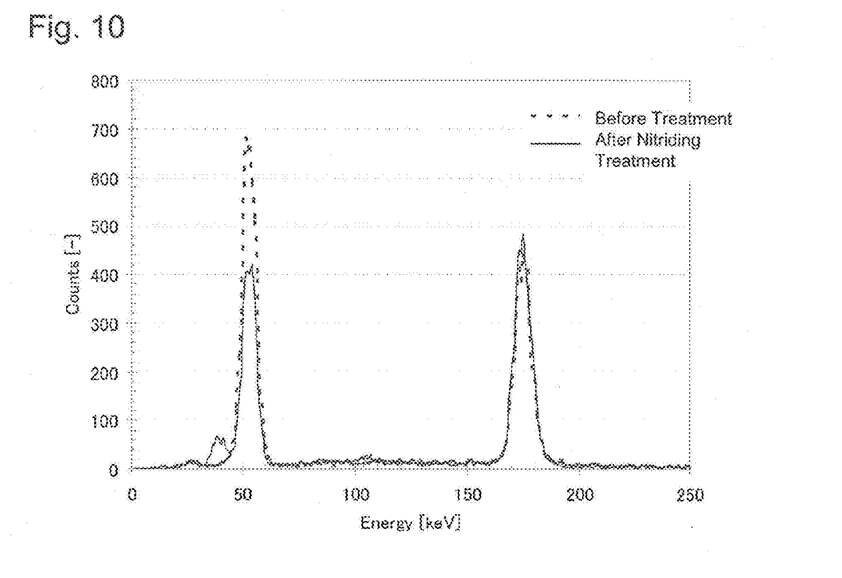
FIG. 10 is a graph showing the results of EDS analysis of the sheet-shaped fiber structure in embodiment 1 before and after the nitriding treatment.

FIG. 10 is a graph showing the results of the energy dispersive X-ray spectrometry (EDS) analysis of the fibers 1 before and after the nitriding treatment. The analysis results are also shown in Table 1 (rounded down to three decimal places).

TABLE 1

|  | Nitrogen (atm %) | Oxygen (atm %) | Silicon (atm %) |
|---|---|---|---|
| Untreated | 0.794 | 60.106 | 39.100 |
| Treated by nitriding | 7.106 | 43.048 | 49.846 |

It is apparent that after the nitriding treatment, the number of nitrogen (N) atoms increases whereas the number of oxygen (O) atoms decreases. Before the nitriding treatment, almost no nitrogen atoms are present in each of the fibers 1, and SiO bonds are dominant on the surface of each of the fibers 1. On the other hand, after the nitriding treatment, SiO bonds and SiN bonds (or Si—O—N bonds) coexist on the surface of each of the fibers 1.

The state of bonds on the surface is more stable when such SiN bonds also exist than when only SiO bonds exist. Specifically, when only SiO bonds exist, the bonds, which are required to be terminated as Si—O—Si siloxane bonds or Si—OH silanol bonds on the uppermost surface, sensitively depend on the atmosphere to which the surface is exposed.

For example, Si—O—Si bonds are thought to be dominant in a high-temperature (e.g., 100° C. or higher) dry atmosphere, whereas Si—OH bonds are thought to be dominant in a low-temperature (e.g., room temperature or lower), high-humidity atmosphere. This is because the reaction shown below tends to occur as a reversible reaction.

Si—OH+Si—OH→←Si—O—Si+$H_2O$

This reaction most easily occurs when two Si—OH groups are spaced adjacent to each other. Therefore, when only $SiO_2$ constitutes the surface, the surface can be unstable depending on the environment. The unstable state, for example, has the effect of varying surface potential. When the surface is made of only $SiO_2$, negatively charged Si—OH bonds and positively charged SiO bonds coexist. Such environmentally variable bonds on the surface mean that the surface potential can easily vary with environment.

As in an example of the present disclosure, when SiN bonds also exist on the uppermost surface, the probability of Si—OH groups existing adjacent to each other decreases, so that the above reaction becomes less likely to occur, in other words, the surface becomes stable. Since the state of bonds on the surface is stable, the surface potential is also stable although it depends on the ratio between the numbers of $NH_2$ and Si—OH groups.

In this example, a blood filter was prepared using the sheet-shaped fiber structure 100 made of the fibers 1 nitrided as described above. The blood filter was subjected to an experiment in which the filter was stored for a certain period of time and how its surface state was changed by the environment was actually examined.

Figure 11:
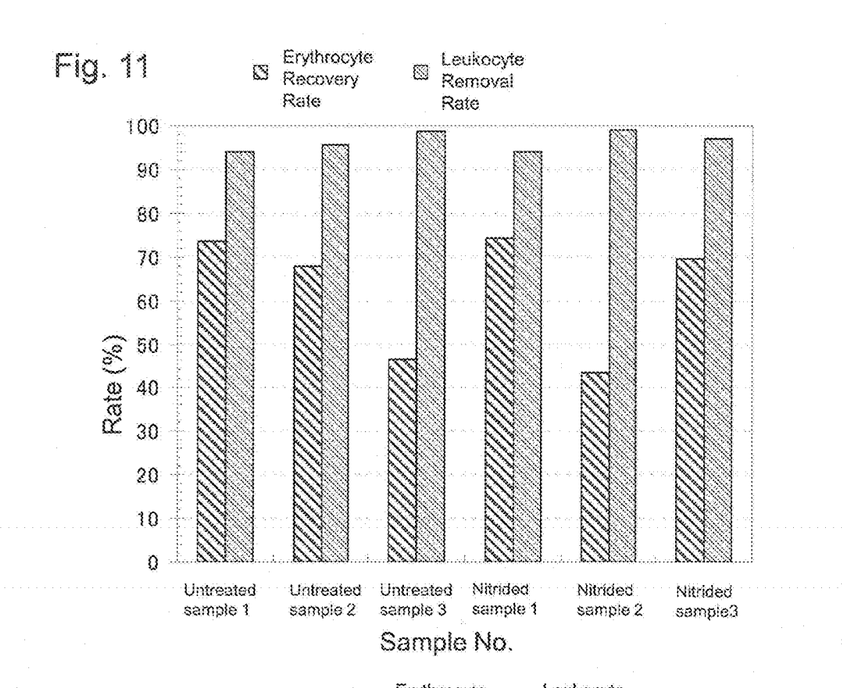
FIG. 11 is a graph showing a comparison between the blood cell separation performances of the non-nitrided sheet-shaped fiber structure and the nitrided sheet-shaped fiber structure in embodiment 1.

FIG. 11 is a graph showing a comparison between the erythrocyte recovery rate (rate of permeation) and the leukocyte removal rate, which were obtained by preparing blood filters using non-nitrided samples (untreated samples 1, 2, and 3) and nitrided samples (nitrided samples 1, 2, and 3) and then filtering a blood sample through each blood filter immediately after the preparation.

Erythrocyte and leukocyte have different surface properties, and leukocyte possesses the property of being more easily captured by the surface of the fibers 1 than erythrocyte. As shown in FIG. 11, the rate of permeation of erythrocytes and the rate of removal of leukocytes are 40 to 70% and 90 to 100%, respectively, with respect to both the non-nitrided samples (untreated samples 1, 2, and 3) and the nitrided samples (nitrided samples 1, 2, and 3), and there was no significant difference observed between them. Thus, it was found that the surface state modification by the nitriding treatment had no effect on the initial properties of the blood filers prepared using the sheet-shaped fiber structure 100.

The blood filter samples were each packaged in a nitrogen atmosphere and stored for a long term. The blood filter samples were then used in the filtration of blood samples in the same manner, and the rate of permeation of erythrocytes and the rate of removal of leukocytes were determined.

Figure 12:
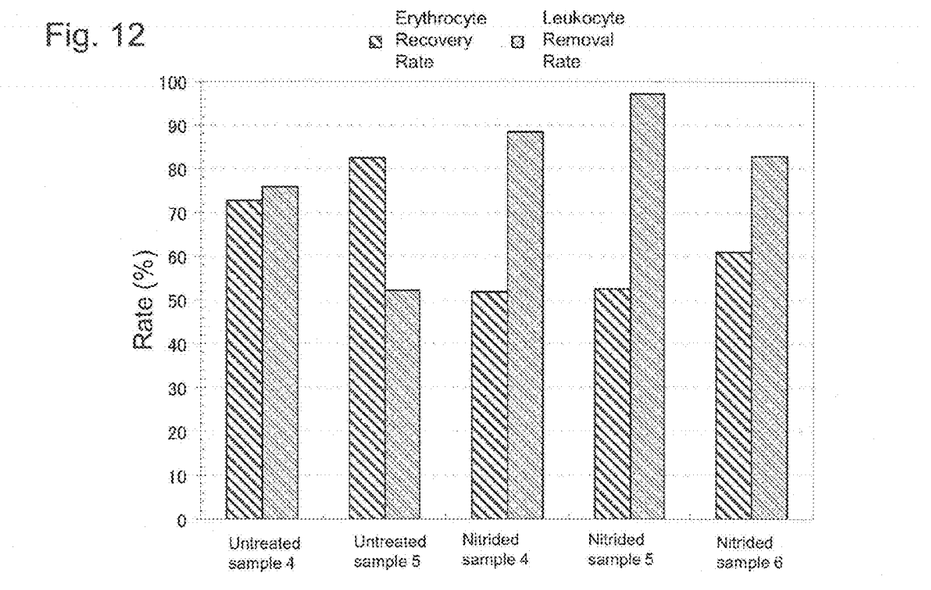
FIG. 12 a graph showing a comparison between the blood cell separation performances of the non-nitrided sheet-shaped fiber structure and the nitrided sheet-shaped fiber structure in embodiment 1 after they are each stored for a long term.

FIG. 12 is a graph showing a comparison between the erythrocyte recovery rate (rate of permeation) and the leukocyte removal rate, which were obtained by storing, for a long term, blood filters of non-nitrided samples (untreated samples 4 and 5) and blood filters of nitrided samples (nitrided samples 4, 5, and 6) and then filtering a blood sample through each blood filter.

When the non-nitrided samples (untreated samples 4 and 5) were used, the leukocyte removal rate decreased, and the rate of permeation of erythrocytes increased, so that the preferential removal of leukocytes, characteristic of the blood filter, became less significant. On the other hand, the nitrided samples (nitrided samples 4, 5, and 6) still had the characteristic of preferentially removing leukocytes although the leukocyte removal rate obtained with them decreased to 80 to 95% of the level of the initial state samples (nitrided samples 1, 2, and 3).

This shows that the nitriding treatment can stabilize the state of bonds on the surface so that the surface characteristics become less likely to degrade even after a long-term storage.

When an $NH_3$ gas atmosphere is used in the doping with nitrogen atoms as described above, it is preferred that nitrogen atoms be absent at and near the most central part (inner part) of each of the fibers 1. In other words, the amount of the nitrogen atom as a dopant has a largest value at the surface of each of the fibers, and the amount of the nitrogen atom as a dopant decreases as it goes to the center, and nitrogen atoms are absent at the most central part. The amount of the dopant continuously changes in this manner. In this case, the molecular structure of each of the fibers 1 does not have any discontinuous points, and therefore, the region doped with nitrogen atoms does not accidentally flake off.

Filter devices made of polymer materials have heat or chemical resistance problems. In contrast, the filter device 101 having the sheet-shaped fiber structure 100 of this embodiment is an inorganic material made of amorphous silicon dioxide and is thus excellent in heat resistance and chemical resistance. The sheet-shaped fiber structure 100, which has a heat resistance temperature of 1,000° C. or higher, can easily undergo a surface treatment or the like performed by a heat treatment. The sheet-shaped fiber structure 100 also has chemical resistance so that it is not corroded by chemicals other than hydrofluoric acid and is also highly resistant to alkaline solutions. Therefore, a filter device 101 having a high porosity per unit area and excellent in heat resistance and chemical resistance can be provided.

(Embodiment 2)

Figure 13:
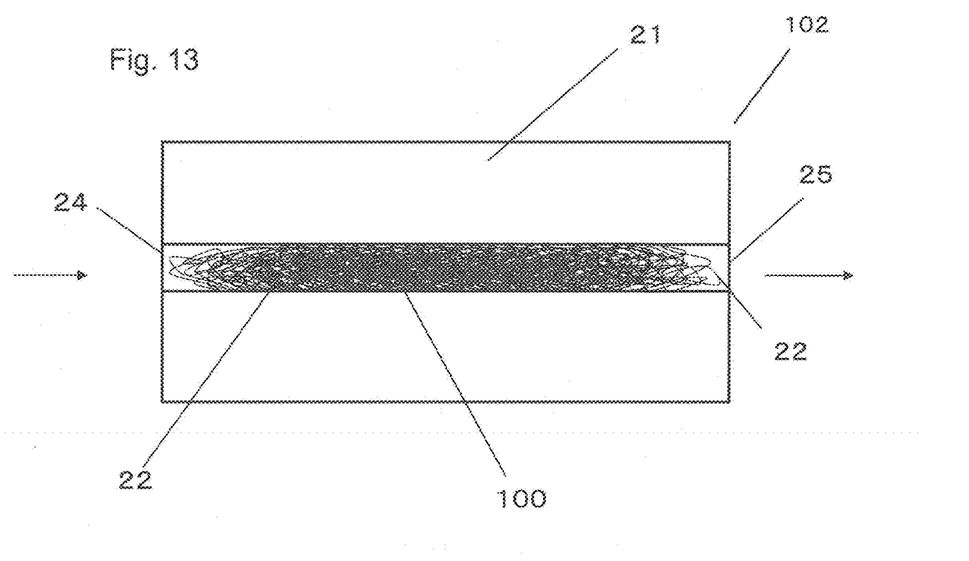
FIG. 13 is a top view of an analysis device in embodiment 2.
Figure 14:
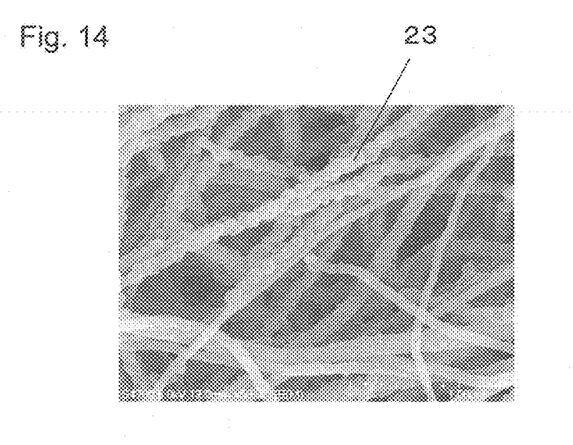
FIG. 14 is a SEM photograph of a principal part of a sheet-shaped fiber structure in embodiment 2.

In this embodiment, an analysis device 102 with the sheet-shaped fiber structure 100 formed in embodiment 1 will be described. FIG. 13 is a top view of the analysis device 102 in embodiment 2. FIG. 14 is a SEM photograph of a principal part of the sheet-shaped fiber structure in embodiment 2.

In this embodiment, the analysis device 102 includes a substrate 21 made of silicon, a flow path 22 formed on the surface of the substrate 21 and having a flow inlet 24 and a flow outlet 25 at its ends, and a sheet-shaped fiber structure 100 packed along the inner wall of the flow path 22 and including fibers 1 made of silicon oxide.

A substrate made of single crystal silicon is used as a substrate 21. Alternatively, for example, a substrate made of an inorganic material such as glass, polycrystalline silicon, thermally oxidized $SiO_2$, polysilicon, or amorphous silicon may be used. Besides silicon, the substrate 21 may also be made of a resin such as polydimethylsiloxane (PDMS), polypropylene, polycarbonate, polyolefin, polyethylene, polystyrene, polyamide, polymethylmethacrylate (PMMA), or cyclic polyolefin, or a composite material of any of these resins and glass.

In this embodiment, the fibers 1 used to form the sheet-shaped fiber structure 100 may be directly bonded to the inner wall of the flow path 22 or packed along the inner wall of the flow path 22. As used herein, the term "directly bonded" means that the fibers 1 are formed directly on the inner wall of the flow path 22, in which the atoms or molecules constituting the fibers 1 and the inner wall of the flow path 22 are directly bonded together (in general, the molecules are covalently bonded). In this example, silicon atoms in the inner wall surface of the flow path 22 are covalently bonded to silicon atoms in the fibers 1 through oxygen atoms from the atmosphere.

As shown in FIG. 14, for example, a functional group 23 may be formed on the surface of each of the fibers 1. The functional group 23 may be any one of an octyl group, an octadecyl group, a docosyl group, and a triacontyl group. Using a silane coupling reaction, such functional groups can be easily formed on the surface of each of the fibers 1.

Immediately before the analysis, the reaction may be performed to form the functional group 23 on the surface of each of the fibers 1 provided on the inner wall of the flow path 22. Alternatively, the functional group 23 may be formed on each of the fibers 1 in advance, and then the fibers 1 may be packed into the flow path 22.

A silane coupling reaction may be performed to form the functional group 23 under conditions where the fibers 1 are formed on the inner wall of the flow path 22. In this case, it is preferred that the unreacted silanol groups remaining after the silane coupling reaction be removed from the surface of each of the fibers 1.

In the analysis device 102 of this embodiment, a sample supplied to the flow pass 22 flows in the arrow direction shown in FIG. 13 and passes through the inside of the flow path 22 while reacting with the functional group 23 formed on the surface of each of the fibers 1 packed along the inner wall of the flow path 22, so that the sample can be analyzed while being subjected to separation.

As shown in FIG. 13, the sample is supplied using the flow inlet 24 provided at the end of the flow path 22. In this time, a fluid control mechanism (not shown) may be provided at the flow inlet 24 so that the sample can be supplied more smoothly. For example, a rotary pump or a plunger pump may be used as the fluid control mechanism.

If an optical path (not shown) for optical analysis is provided at the flow outlet 25 at the end of the flow path 22, separated materials can be detected immediately after being separated. Therefore, an optical path for optical analysis is preferably provided at the flow outlet 25.

Next, advantageous effects of the analysis device 102 in this embodiment will be shown.

The sheet-shaped fiber structure 100 used in the analysis device 102 of this embodiment includes the fibers 1 each having a diameter of 0.01 to 1 μm. This feature makes it possible to keep the surface area large enough to provide higher separation function and sensitivity. The diameter of each of the fibers 1 may be smaller than that of a usual filler such as silica gel. Therefore, the fibers 1 can be densely packed along the inner wall of the flow path 22, so that the analysis device 102 can be made smaller. Therefore, even a very small amount of a sample can be analyzed using a small amount of a solvent, such as acetonitrile, for the separation. Thus, the amount of solvents for separation can be reduced. This makes it possible to reduce the time for analysis and the solvent required for separation and to improve analysis efficiency.

The analysis device 102 of this embodiment may be used as a solid phase for adsorption chromatography, partition chromatography, ion-exchange chromatography, molecular exclusion chromatography, affinity chromatography, etc. The analysis device 102 may also be used for gas chromatography, liquid chromatography, supercritical fluid chromatography, etc.

The embodiment shows an example where the flow path 22 is formed on the substrate 21. However, the flow path 22 does not always have to be formed on the substrate 21. Alternatively, the flow path 22 may be in the form of a capillary (not shown), and the sheet-shaped fiber structure 100 including the fibers 1 each having the functional group 23 may be provided along the inner wall of the flow path 22. Such a device can also be used.

This embodiment shows an example where a single linear flow path 22 is formed on the substrate 21. However, how the flow path 22 is shaped or how many flow paths are formed is not limited to that shown above as long as the flow inlet 24 and the flow outlet 25 are formed at the ends of the flow path 22.

In this embodiment, the sample is supplied using a fluid control mechanism. Alternatively, the sample may be supplied to the flow path 22 by sucking from the flow outlet 25.

A water-repellent film is formed by performing a water-repellent treatment on the sheet-shaped fiber structure 100 as well as embodiment 1, so that the same advantageous effect is exerted.

The fibers 1 of the sheet-shaped fiber structure 100 may be subjected to a nitriding treatment in which doping with nitrogen atoms is performed from the surface part of each of the fibers 1 as well as embodiment 1, so that the molecular composition of the surface of each of the fibers 1 can be modified. Specifically, the surface of each of the fibers 1 can include SiN bonds or SiON bonds. In this case, the same advantageous effect is also exerted.

(Embodiment 3)

In this embodiment, an analysis device 102 with the sheet-shaped fiber structure 100 formed in embodiment 1 will be described. In this embodiment, the analysis device 102 as a single device includes a plurality of sheet-shaped fiber structures 100 having different functions.

Figure 15:
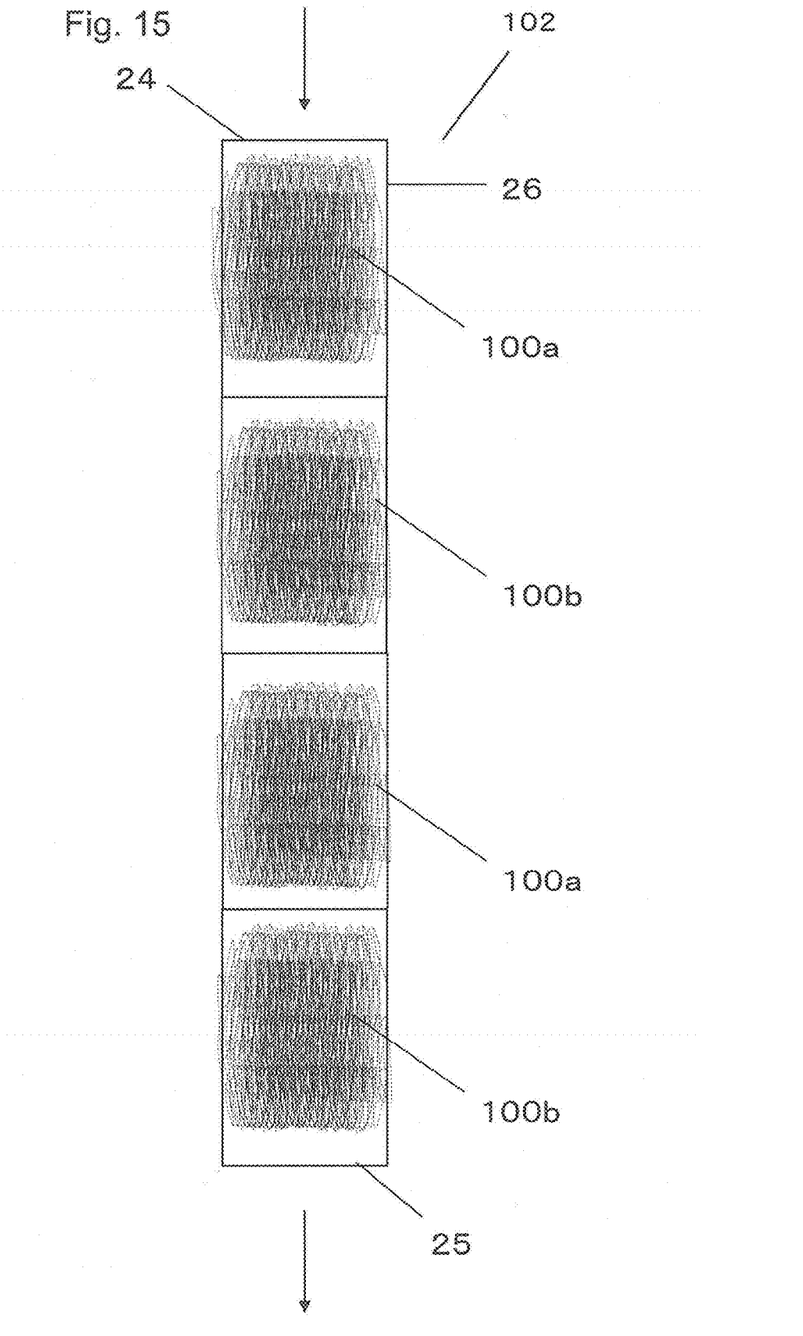
FIG. 15 is a cross-sectional view showing use of a filter device in embodiment 3.

FIG. 15 is a cross-sectional view showing the analysis device 102 in this embodiment. The analysis device 102 includes a capillary 26 having a flow inlet 24, a flow outlet 25, and a flow path 22 connected between them; and sheet-shaped fiber structures 100 each packed along the inner wall of the flow path 22 of the capillary 26 and including fibers 1 made of silicon oxide. The sheet-shaped fiber structures 100 are placed at a plurality of locations in the flow path 22. The plurality of sheet-shaped fiber structures 100 include first sheet-shaped fiber structures 100a each coated hydrophilically and second sheet-shaped fiber structures 100b each coated hydrophobically. The first and second sheet-shaped fiber structures 100a and 100b are alternately stacked.

The first sheet-shaped fiber structure 100a can be obtained by hydrophilically coating the surface of each of the fibers. To coat the surface of each of the fibers 1 hydrophilically, the surface made of silicon oxide may be treated in such a manner that Si—OH bonds are mainly formed, so that the product has hydrophilicity.

When the hydrophilic coating is made, the hydrophilicity can be made further uniform in the interior of the sheet-shaped fiber structure, which makes it possible to improve the analytical precision.

On the other hand, the second sheet-shaped fiber structure 100b can be obtained by hydrophobically coating the surface of each of the fiber 1. The hydrophobic coating, for example, may be performed in such a manner that Si—O bonds are mainly formed, so that the product has hydrophobicity. In addition to this method, a water-repellent treatment may also be performed by the method described for embodiment 1.

The sheet-shaped fiber structure 100 of the present disclosure has a large surface area. Therefore, the surface function such as hydrophilicity or water repellency can be made stronger by controlling the ratio between SiOH bonds for hydrophilicity and SiO bonds for water repellency. The sheet-shaped fiber structure 100 includes a plurality of fibers 1 that are tangled and connected together to form large voids in the interior. Therefore, a hydrophilic space and a water-repellent space can be continuously connected only by modifying the surface molecular structure.

Since the fibers 1 of the sheet-shaped fiber structure 100 are made of silicon oxide, the fibers 1 can easily undergo chemical modification. Therefore, the first and second sheet-shaped fiber structures 100a and 100b can be easily formed.

When a plurality of sheet-shaped fiber structures 100 having different functions are formed in a single analysis device 102 as shown above, the time in which a solvent material travels each region can be more significantly changed, so that separation and analysis can be easily performed for any purpose. This makes it possible to perform analysis more efficiently.

In this embodiment, for example, the first and second sheet-shaped fiber structures 100a and 100b are alternately stacked in four layers. Alternatively, the first and second sheet-shaped fiber structures 100a and 100b may be alternately stacked in two layers.

In this embodiment, hydrophilically coated fibers 1 and hydrophobically coated fibers 1 are used in the first and second sheet-shaped fiber structures 100a and 100b, respectively. Alternatively, for example, fibers 1 coated with an ion-exchange membrane capable of performing ion exchange may also be used to form the sheet-shaped fiber structure 100.

For example, the fibers 1 coated with an ion-exchange membrane capable of performing ion exchange can be obtained by forming, on the fibers 1, functional groups having different valences, dissociabilities, or other properties. Using such a sheet-shaped fiber structure 100, ion-exchange chromatography can be easily performed.

Alternatively, fibers 1 having a density gradient may also be used to form the sheet-shaped fiber structure 100.

When the sheet-shaped fiber structure 100 is formed, the fibers 1 having a density gradient can be obtained by controlling the void size in such a manner that the void size is gradually decreased in the direction from the upstream part to the downstream part of the sheet-shaped fiber structure 100. Using this sheet-shaped fiber structure 100, molecular exclusion chromatography can be easily performed.

When a plurality of such sheet-shaped fiber structures 100 having different purposes are used, different analyses can be performed using a single analysis device.

As shown above, for example, the sheet-shaped fiber structure according to the present disclosure is used to form a filter device for extracting or separating erythrocytes from human or animal whole blood or a solution derived from a living body, or used to form an analysis device for chromatography or the like.

What is claimed is:

1. A filter device including at least a sheet-shaped fiber structure having a plurality of fibers made of amorphous silicon dioxide, wherein the plurality of fibers are tangled and thus connected together to form voids in the sheet-shaped fiber structure, and
    at least a surface part of each of the fibers is doped with a nitrogen atom.

2. The filter device according to claim 1, wherein the sheet-shaped fiber structure has connection sites formed by partially bonded fibers, and the fibers are partially bonded together at partially fused fibers.

3. The filter device according to claim 1, wherein each of the fibers has a length of 1 µm or more and 500 µm or less.

4. The filter device according to claim 1, wherein a maximum distance between the fibers adjacent to each other is 1 µm or more and 50 µm or less.

5. The filter device according to claim 1, wherein each of the fibers has a diameter of 0.01 µm or more and 1 µm or less.

6. The filter device according to claim 1, wherein each of the fibers has a surface modified with a water-repellent film.

7. The filter device according to claim 1, wherein the concentration of the nitrogen atom dopant is the highest at the surface part and decreases as it goes to a central part of each of the fibers, and the nitrogen atom is absent at least at and near a most central part of each of the fibers.

8. An analysis device comprising:
    a flow path;
    a filter device provided in the flow path, wherein the filter device including at least a sheet-shaped fiber structure having a plurality of fibers made of amorphous silicon dioxide, wherein the plurality of fibers are tangled and thus connected together to form voids in the sheet-shaped fiber structure; and
    a plurality of the sheet-shaped fiber structures,
    wherein
    the plurality of the sheet-shaped fiber structures include:
        a first sheet-shaped fiber structure coated hydrophilically; and
        a second sheet-shaped fiber structure coated hydrophobically, and
    the first and second sheet-shaped fiber structures are alternately stacked.

9. The analysis device according to claim 8, wherein the sheet-shaped fiber structure has a functional group formed on a surface thereof, and
    the functional group is selected from a group of an octyl group, an octadecyl group, a docosyl group, and a triacontyl group.

10. The analysis device according to claim 8, wherein the flow path has a diameter of 10 µm to 1,000 µm.

11. The analysis device according to claim 8, wherein the flow path has a flow inlet provided with a fluid control mechanism.

12. The analysis device according to claim 8, wherein the flow path has an end part provided with an optical path for optical analysis.

* * * * *